United States Patent [19]

Jahnke et al.

[11] Patent Number: 4,946,965
[45] Date of Patent: Aug. 7, 1990

[54] PROCESS FOR DRYING SOLID PHOTOGRAPHIC ADDENDA

[75] Inventors: Frank M. Jahnke, Rochester; Carl B. Richenberg, Batavia, both of N.Y.

[73] Assignee: Eastman Kodak Company, Rochester, N.Y.

[21] Appl. No.: 469,703

[22] Filed: Jan. 23, 1990

Related U.S. Application Data

[63] Continuation-in-part of Ser. No. 313,557, Feb. 22, 1989, abandoned.

[51] Int. Cl.$^5$ ............... C07D 231/22; C07C 235/00; C07C 235/38
[52] U.S. Cl. .................... 548/365; 564/153; 430/543; 430/554; 430/556
[58] Field of Search ................ 548/365; 564/153

[56] References Cited

U.S. PATENT DOCUMENTS

| | | | |
|---|---|---|---|
| 3,966,981 | 3/1976 | Schultz | 426/425 |
| 3,969,196 | 5/1976 | Zosel | 203/49 |
| 4,250,331 | 7/1981 | Shimshick | 562/485 |
| 4,308,200 | 11/1981 | Fremont | 530/202 |
| 4,632,837 | 8/1986 | Schutz | 426/425 |

FOREIGN PATENT DOCUMENTS

61/046202 5/1986 Japan.

Primary Examiner—Mukund J. Shah
Assistant Examiner—Philip I. Datlow
Attorney, Agent, or Firm—Alfred P. Lorenzo

[57] ABSTRACT

Solid photographic addenda, such as photographic color couplers or sensitizing dyes, which are wet with occluded organic liquid, after being subjected, for example, to processes such as crystallization or washing, are contacted with an extractant composed of carbon dioxide in liquid form or in the form of a supercritical fluid to remove the organic liquid. The process is capable of use with any solid photographic addendum which is insoluble in the extractant and any organic liquid which is soluble in the extractant. It can be completed much more quickly than conventional processes in which such solids are dried with the aid of heat and/or vacuum, while effectively avoiding problems of clumping and thermal degradation which commonly occur in dryers. It provides a product that is capable of meeting the demanding requirements of the photographic art with respect to both physical and chemical characteristics.

12 Claims, 3 Drawing Sheets

PROCESS FOR DRYING SOLID PHOTOGRAPHIC ADDENDA

CROSS-REFERENCE TO RELATED APPLICATIONS

This is a continuation-in-part of application Ser. No. 313,557 filed Feb. 22, 1989 now abandoned.

FIELD OF THE INVENTION

This invention relates in general to photography and in particular to the use of solid addenda in the preparation of photographic emulsions and other photographic coating compositions. More specifically, this invention relates to a process of removing occluded organic liquid from solid photographic addenda prior to the use of such addenda in the manufacture of photographic materials.

BACKGROUND OF THE INVENTION

In the manufacture of photographic emulsions, and other photographic coating compositions, a wide range of chemical agents are incorporated in the emulsion, or other coating composition, to provide particular functions and benefits. These agents, which are typically utilized in solid form, are commonly referred to as "photographic addenda", i.e., addenda useful in image-recording systems employing photographic processes. They include such materials as color couplers, sensitizing dyes, desensitizing dyes, pigments, brightening agents, developing agents, development inhibitors, antifoggants, stabilizers, hardeners, ultraviolet absorbers, photoconductors, chemical sensitizers, antistatic agents, dye-releasers, and the like.

Prior to their use in the preparation of photographic emulsions and/or other photographic coating compositions, it is frequently necessary to subject solid photographic addenda to a drying process to remove occluded organic liquid. Such organic liquid remains in and on the solid particles after such processing steps as crystallization and washing. Many common organic liquids are involved, with typical examples including acetic acid, acetone, acetonitrile, dimethylformamide, ethyl acetate, heptane, isopropyl alcohol, methanol, methylene chloride, n-propyl acetate, pyridine, toluene, triethylamine and xylenes.

Conventionally, solid photographic addenda are dried by heat or vacuum or both in equipment such as tray dryers, rotary-cone dryers or rotary processors. Each of these processes relies on evaporation of the liquid remaining in or on the solid material. Usually, heat is supplied to maintain high partial pressures of the liquid whose removal is desired, to thereby ensure adequate drying rates. Hence, effective heat transfer from the dryer to the solids is of tantamount importance for solids to be dried in this manner. Surface area to volume ratios of large-scale dryers used in production are typically much smaller than in laboratory-scale models; hence production drying times are much longer than found in the laboratory.

The morphology of the conventionally-dried product can be a very serious problem. Balling and clumping of solids in dryers is common, which is detrimental not only because this reduces drying rates, but also because the size of dried solid is often not suitable. Another operation, where the average particle size of the material is reduced so that it dissolves more rapidly in a subsequent processing step, such as preparation of a photographic dispersion, is often required.

Thermal degradation of heat-sensitive materials also occurs in conventional dryers. In this case, off-specification material is produced, and the batch must be discarded or reworked to eliminate the degradation products.

The time required for conventional drying of solid photographic addenda is often prolonged, and this adds greatly to manufacturing costs. For example, with conventional rotary-cone units, some commercially important color couplers require a drying time of as long as four weeks.

Conventional dryers typically have no built-in pollution control devices and thus require added equipment to prevent the emission of potentially hazardous solvents from the production facility.

It is toward the objective of providing a new process for the removal of occluded organic liquid from solid photographic addenda, which can be carried out easily and expeditiously, which does not impair the morphology of the product nor subject it to thermal degradation, and which avoids the emission of potentially hazardous solvents, that the present invention is directed.

SUMMARY OF THE INVENTION

In accordance with this invention, solid photographic addenda such as color couplers, sensitizing dyes and the like, which are wet with occluded organic liquid, after being subjected to processes such as crystallization, washing and the like, are contacted with an extractant, composed of carbon dioxide in liquid form or in the form of a supercritical fluid, to remove the organic liquid. The process is capable of use with any solid photographic addendum which is insoluble in the extractant and with any occluded organic liquid which is soluble in the extractant. It is not suitable for removal of water from solid photographic addenda, because of the immiscibility of water with the extractant.

Thus, the process of this invention includes the steps of (1) contacting a solid photographic addendum in particulate form with an extractant composed of carbon dioxide in liquid form or in the form of a supercritical fluid for a time sufficient to extract the organic liquid, the solid addendum being insoluble in the extractant and the organic liquid being soluble in the extractant, and (2) recovering the solid addendum in a substantially dry state. Suitable methods for contacting the wet solid with the extractant include agitation in a stirred tank, percolation through a packed bed, and ebullition in a fluidized bed.

In a preferred embodiment, the process includes the steps of (3) separating the organic liquid from the extractant and (4) recycling the extractant to step (1).

DESCRIPTION OF THE PREFERRED EMBODIMENTS

As indicated above, the method of this invention is based on the use of carbon dioxide as an extractant. The carbon dioxide can be used in liquid form or in the form of a supercritical fluid, that is, a fluid existing at temperatures and pressures exceeding the critical point.

It has been known heretofore to employ an extractant composed of carbon dioxide in liquid form or in the form of a supercritical fluid. Included among the numerous patents related to such use of carbon dioxide are Roselius et al, U.S. Pat. No. 3,923,847 issued Dec. 2, 1975, relating to the production of cocoa butter by treatment of cocoa products with supercritical carbon dioxide; Schwengers, U.S. Pat. No. 3,939,281 issued Feb. 17, 1976, relating to the removal of fat from starch-containing vegetable material by use of carbon dioxide of other gases in a supercritical state; Schultz, U.S. Pat. No. 3,966,981 issued June 29, 1976, relating to the removal of residual hexane from de-fatted soybeans by extraction with liquid carbon dioxide; Zosel, U.S. Pat. No. 3,969,196, issued July 13, 1976 relating to the separation of mixtures of organic compounds using a gas such as carbon dioxide maintained under supercritical conditions of temperature and pressure; Modell, U.S. Pat. No. 4,061,566 issued Dec. 6, 1977 relating to removal of an adsorbate from a polymeric adsorbent by contact with carbon dioxide or other gas in the form of a supercritical fluid; Shimshick, U.S. Pat. No. 4,250,331 issued Feb. 10, 1981 relating to the use of supercritical carbon dioxide to recover carboxylic acids from dilute aqueous solutions of alkali metal salts of such acids; Fremont, U.S. Pat. No. 4,308,200, issued Dec. 29, 1981, relating to the extraction of tall oil and turpentine from coniferous wood by treatment with supercritical carbon dioxide; Stahl et al, U.S. Pat. No. 4,548,755 issued Oct. 22, 1985 relating to the extractive production of natural waxes from vegetable or animal starting material using carbon dioxide or other gases in a supercritical state; and Schultz et al, U.S. Pat. No. 4,632,837 issued Dec. 30, 1986 relating to the production of concentrated extracts from fresh plants by extraction with carbon dioxide at supercritical pressure.

While the prior art has proposed a wide variety of different uses for carbon dioxide in liquid form or in the form of a supercritical fluid, there has been no suggestion of its use for removal of residula organic liquids from solid photographic addenda. Moreover, it would not have been expected that this extractant would provide photographic addenda meeting strict specifications for dryness in the very short time that is achievable, nor that the extraction process would not impair the photographic performance of the addenda, nor that the resulting products would have morphological and other characteristics that render them especially suitable for use in the extremely demanding environment of photographic manufacturing operations.

As indicated hereinabove, in the process of this invention, the organic liquid must be soluble in the extractant. Solubility provides the driving force for removal of the organic liquid from a solid matrix. The maximum driving force, and thereby optimum performance, is achieved when the organic liquid is fully miscible with the carbon dioxide. Also, the solid photographic addendum must be insoluble in the carbon dioxide to permit separation of the organic liquid from the solid particles.

Carbon dioxide in the form of a liquid, or a supercritical fluid, does not dissolve high molecular weight compounds such as photographic color couplers and photographic sensitizing dyes, nor does it dissolve highly polar compounds such as water. However, it is very effective in dissolving many common organic solvents such as are used in processes for synthesis of solid photographic addenda. It is also capable of dissolving many of the lower molecular weight impurities associated with solid photographic addenda, and thereby serving to combine the functions of drying and purification in a single process.

In many synthetic processes, drying is the final step in the separation and isolation train in the production of solid chemical intermediates and products. By the term "drying" is meant the removal of the aqueous or organic liquid remaining in and around solid particles after processing steps such as crystallization or washing. Thus, the method of this invention serves as an alternative to conventional drying processes when the occluded liquid is an organic liquid that is soluble in carbon dioxide. It can, in some instances, serve not only as a superior alternative to conventional drying, but also as a means of producing a purer product which is significantly better for photographic use.

The process of this invention can be carried out by use of either liquid carbon dioxide or supercritical carbon dioxide. The choice of which of these to use is dependent on a variety of factors including the specific solids and liquids involved and the particular equipment employed.

The removal of organic liquid from solid photographic addenda by the process of this invention can be characterized as a two-step process. The first step is a displacement process in which the organic liquid on the exterior surfaces of the solid particles is removed. In the second step, organic liquid diffuses from within the solid particles into the stream of carbon dioxide flowing past these particles. The rate at which the displacement step proceeds depends on the solubility of the organic liquid in the carbon dioxide, the ratio of the viscosity of the organic liquid to that of the carbon dioxide, and the pore structure of the solid particles. The rate at which the organic liquid within the particles is extracted depends on the solubility of the organic liquid in the carbon dioxide, the diffusion coefficient of the organic liquid in carbon dioxide, the partitioning of the organic liquid between the solid and carbon dioxide phases, and the mass transfer coefficient between the carbon dioxide and the solid particles.

The organic liquids extracted from solid photographic addenda by the process of this invention are soluble in carbon dioxide in either the liquid or supercritical fluid states. Also, the pore structure of the solid remains the same whether it is invaded by either a liquid or a supercritical fluid. Hence, any difference in the rate of extraction that is dependent on whether the carbon dioxide extractant is in liquid form or supercritical fluid form is a function of the other properties listed above. It can be shown experimentally that the step limiting the rate of removal of organic liquid, in reaching the specifications involved with solid photographic addenda, is the diffusion of organic liquid from pores within the solid.

In general, the diffusion coefficient $D$ of a solute in condensed matter increases with increasing temperature $T$ or decreasing viscosity $\mu$ of the phase in which the solute is dissolved. This is summarized by the Stokes-Einstein equation, $$D = \frac{\phi T}{\mu}$$

where $\phi$ is a constant for a given solute. The viscosity of carbon dioxide, in turn, increases with increasing density. For definiteness, consider a case where the pressure of a carbon dioxide stream is held constant at 81.6 atmospheres, and the temperature is varied between 25° C., where carbon dioxide is a liquid, and 35° C., where carbon dioxide is a supercritical fluid. At the lower temperature, the density is 0.9 g/cm$^3$, whereas at the upper temperature, the density is 0.5 g/cm$^3$. Hence the diffusion coefficient increases when the temperature is raised from 25° C. to 35° C. This implies that the extraction rate should increase.

The mass transfer coefficient around the particles is a function of the diffusivity D and the mass-transfer boundary layer thickness, which is in turn a function of viscosity and the velocity of the carbon dioxide. Referring to the example cited above, for a constant fluid velocity the mass-transfer coefficient should increase, so that the particles release the solute more quickly.

The remaining variable is the adsorption of the solute onto the surface of the solid. For a given solid, solute and carrier fluid, as the temperature of the system is raised, the adsorption decreases. Based on tests in which photographic addenda wet with organic liquid have been extracted at 81.6 atmospheres with either 25° C. or 35° C. carbon dioxide, it has been found that the extraction rate is nearly identical. Using a chromatographic method, the Henry's Law slope was measured at the above conditions for a color coupler hereinafter identified as Coupler Y-1, wet with heptane and with toluene. This confirmed that the adsorption did indeed increase with increasing temperature, leading to the surprising conclusion that the increase in adsorption balances the increase in solute diffusivity.

The implication of this observation is that the state of the carbon dioxide, that is either liquid or supercritical fluid, is not crucial in determining the rate of extraction if carbon dioxide devoid of organic liquid is introduced into the extractor, because the temperature affects the parameters controlling the extraction in a balancing manner.

The time required to carry out the process of this invention varies greatly, depending on such factors as the particular organic liquid which is being removed, the particular solid involved, the amount of occluded organic liquid initially present and the desired level in the final product, the temperature, the pressure, and the efficiency of the contacting apparatus. Thus, times can vary from a few minutes to several hours. However, in general, times are orders of magnitude shorter than can be achieved with conventional processes for drying photographic addenda, many of which are heat-sensitive and must be handled with great care to retain optimum photographic performance.

The extraction apparatus employed in the process of this invention is adapted to withstand the pressure exerted by the carbon dioxide extractant. The temperature at which the apparatus is maintained is the same as the temperature of the carbon dioxide extractant unless heating or cooling of the carbon dioxide extractant by the walls of the apparatus is desired, in which case a temperature differential will exist by virtue of the heat transfer between the walls and the flowing fluid.

In a preferred embodiment of the process of this invention, the amount of occluded organic liquid is in the range of from about 0.04 parts to about 2 parts per part by weight of the solid, and the process is continued for a time sufficient to remove the occluded organic liquid to a level of less than 0.02 and preferably less than 0.01 parts per part by weight of the solid.

The supercritical fluid region is defined as that region of temperatures and pressures greater than or equal to the critical temperature and critical pressure. The density, viscosity and diffusivity of supercritical fluids are intermediate between those of a liquid and a gas. For carbon dioxide, as for other supercritical fluids, such properties vary greatly with variation in temperature and pressure near the critical point. The critical temperature of carbon dioxide is 304.2° K. (31.0° C.) and the critical pressure is 72.9 atmospheres. At the critical point, the density is 0.468 g/cc.

Carbon dioxide has many significant advantages for use in the process described herein. It is inexpensive, inert, nontoxic and nonhazardous. Moreover, in using carbon dioxide in the process of this invention, there is no contamination of the product, which is critically important for photographic addenda. While high pressure equipment is needed, the added costs of such equipment are more than offset by the lower energy costs compared to conventional processes for drying photographic addenda, and by the tremendous throughput capability that comes about as a consequence of the very short drying times that are possible. A single extraction unit of the type described herein is capable of replacing several air or vacuum ovens, and thereby conserving valuable space which is critically needed in photographic manufacturing plants.

Preferably, in the process of this invention, the carbon dioxide is recovered. Thus, the preferred embodiment of the invention includes the steps of separating the organic liquid from the carbon dioxide and recycling the carbon dioxide to the first step of the process. Thus, the overall process comprises an extraction stage and a separation stage. In the extraction stage, the extractant, i.e., the carbon dioxide, dissolves the organic liquid. In the separation stage, the resulting solution is separated into organic liquid and carbon dioxide. Any of many well known processes can be used to achieve this result, including processes of evaporation, adsorption, absorption or fractional distillation.

The separation stage can be pressure-controlled or temperature-controlled. In a pressure-controlled process, the solution is expanded in the separation stage to precipitate the organic liquid and the carbon dioxide is recompressed for recycle. In the temperature-controlled process, the solution is heated to lower the density of the carbon dioxide and thereby precipitate the organic liquid. The density of the carbon dioxide is then increased for recycle by isobaric cooling.

Pressures favorable for the separation are in the range of from about 25 to about 70 atmospheres, while temperatures dictated by an adiabatic expansion of the stream are suitable. With highly volatile organic solvents, use of a pressure-controlled process is most practical.

As an alternative to the use of a pressure-controlled or temperature-controlled separation stage, the organic liquid can be separated from the carbon dioxide by use of a suitable membrane. The membrane separation can be operated in the supercritical region of temperature and pressure and thereby permit recovery of the organic liquid without depressurizing the solution or altering the temperature. This provides for a substantial savings in capital and operating costs. Suitable membrane processes include reverse osmosis and ultrafiltration. The membrane is selected with a suitable pore size to hold back the organic liquid but allow the carbon dioxide to pass through freely. The carbon dioxide passing through the membrane can be recycled directly to the first step of the process without depressurizing.

Use of membrane separation processes with supercritical fluids is described in Japanese Patent Publications No. 62/129102, published June 11, 1987 and No. 62/158223, published July 14, 1987.

As discussed hereinabove in considerable detail, the process of this invention can be carried out using liquid carbon dioxide or using supercritical carbon dioxide. An advantage of using liquid carbon dioxide is that somewhat lower pressures can be employed. A further advantage of using liquid carbon dioxide is that the specification of organics can be raised in the stream that is returned from the separation section of the process. This results from the lowered adsorption of the solute on the solid. An advantage of using supercritical carbon dioxide is that it is capable of dissolving species of higher molecular weight than those that are dissolved by liquid carbon dioxide. This permits the use of a wider range of organic liquids in processing solid photographic addenda. It also permits the removal of a greater variety of impurities from the solid photographic addenda.

As indicated hereinabove, the process of this invention is useful with any solid photographic addendum which is insoluble in carbon dioxide in the form of a liquid or a supercritical fluid. Such materials are well known to those skilled in the photographic art. Photographic addenda are described in detail in an article entitled, "Photographic Silver Halide Emulsions, Preparations, Addenda, Processing And Systems", Research Disclosure, Item 17643, Volume 176, Dec. 1978. This article is incorporated herein by reference.

The process of this invention is of particular benefit for use with one or more of the following specific classes of photographic addenda:
(1) cyan-dye-forming couplers;
(2) magenta-dye-forming couplers;
(3) yellow-dye-forming couplers;
(4) ultraviolet absorbing compounds such as thiazolidones, benzotriazoles, methine dyes and 1-amino-4-cyano-1,3-butadienes;
(5) photographic dyes, including sensitizing dyes, desensitizing dyes, anti-halation dyes and filter dyes, such as the cyanines, merocyanines, complex cyanines and merocyanines (i.e., tri-, tetra-, and polynuclear cyanines and merocyanines), oxonols, hemioxonols, styryls, merostyryls and streptocyanines; and
(6) brightening agents such as stilbenes, triazines, imidazolones, pyrazolines, triazoles, coumarins, acetylenes, oxazoles and oxadiazoles.

Couplers which form cyan dyes upon reaction with oxidized color developing agents are described in such representative U.S. Pat. as Nos. 2,474,293; 2,772,162; 2,801,171; 2,895,826; 3,002,836; 3,419,390; 3,476,563; 3,779,763; 3,996,253; 4,124,396; 4,248,962; 4,254,212; 4,296,200; 4,333,999; 4,443,536; 4,457,559; 4,500,635 and 4,526,864, the disclosures of which are incorporated herein by reference.

Preferred cyan coupler structures are phenols and naphthols which form cyan dyes on reaction with oxidized color developing agent. These preferred structures include the following:

where $R^4$ represents a ballast group, $R^5$ represents one or more halogen atoms (e.g., chloro, fluoro), lower alkyl (e.g., methyl, ethyl, butyl) or lower alkoxy (e.g., methoxy, ethoxy, butoxy) groups and X is hydrogen or a coupling off group.

Couplers which form magenta dyes upon reaction with oxidized color developing agents are described in such representative patents and publications as: U.S. Pat. Nos. 1,969,479; 2,311,082; 2,343,703; 2,369,489; 2,600,788; 2,908,573; 3,061,432; 3,062,653; 3,152,896; 3,519,429; 3,725,067; 4,120,723; 4,500,630; 4,540,654 and 4,581,326; and European Patent Publication Nos. 170,164 and 177,765; the disclosures of which are incorporated herein by reference.

Preferred magenta couplers include pyrazolone compounds having the structural formulae:

and

-continued pyrazolotriazole compounds having the structural formulae:

and pyrazolobenzimidazole compounds having the structural formulae:

and and indazole compounds having the structural formula:

wherein
X is as defined above;
$R^4$ is a ballast group;
$R^6$ is halogen (e.g., chloro, fluoro), alkyl or alkoxy having from 1 to 4 carbon atoms, phenyl or substituted phenyl (e.g., 2,4,6-trihalophenyl);
$R^7$ is hydrogen or a monovalent organic radical, for example a saturated or unsaturated alkyl group having from 1 to about 20 carbon atoms (methyl, ethyl, propyl, butyl, decyl, dodecyl, heptadecyl, octadecyl); a cycloalkyl group (e.g. cyclohexyl); an aralkyl group (e.g. benzyl); an aryl group (e.g. phenyl, alkoxyphenyl in which the alkyl or alkoxy radical has from 1 to about 20 carbon atoms, nitrophenyl, aminophenyl, acylaminophenyl, alkylaminophenyl, naphthyl, diphenyl, diphenylether, diphenylthioether); a heterocyclic group (e.g. α-furyl, α-benzofuryl, α-pyridyl); an amino, hydroxy or carboxylic acid group, it being possible for the hydrogen atoms of these groups to be substituted, for instance by a mono- or dialkylamino group in which the alkyl groups have from 1 to about 20 carbon atoms; a cycloalkylamino group; an amino group in which one hydrogen atom is replaced by a pyrazolo-[1,5-a]-benzimidazolyl radical which is bonded in 3- position to said nitrogen atom so that couplers result in which two pyrazolo-[1,5-a]-benzimidazolyl radicals are connected by an amino group, and in which the remaining hydrogen atom may be replaced by a substituent such as an alkyl-, aryl-, aralkyl- or acyl- radical; an acylamino group in which the acyl radical is derived from an aliphatic, aromatic or heterocyclic carboxylic acid; a carboxylic acid group which is esterified by means of an aliphatic, cycloaliphatic or aromatic alcohol or by an aromatic compound having a phenolic hydroxy group; or a carboxyamido group in which the amido group may be substituted for example by a saturated or unsaturated alkyl, aralkyl, aryl or heterocyclic group;

$R^8$ represents a hydrogen atom, a sulphonic acid or a carboxylic acid group; a halogen atom (e.g. chlorine or bromine); or an azo radical $-N=NR^{13}$, wherein $R^{13}$ can be an aromatic or heterocyclic radical (phenyl, naphthyl, diphenyl, diphenylether, benzthiazolyl, pyridyl, quinolyl or pyrazolyl) which may be substituted such as by an alkyl group having from 1 to about 20 carbon atoms, hydroxy, alkoxy, halogen, amino, substituted amino, nitro, sulphonic acid or carboxylic acid groups;

$R^9$ represents a divalent radical such as wherein $R^{10}$ can be alkyl, aralkyl, especially phenyl, phenyl substituted preferably in the p-position by a tertiary amino group such as a dialkylamino group in which at least one of the alkyl groups is substituted by carboxy, sulpho, hydroxy, alkoxy, carboxylalkyl, cyano or the divalent radical wherein $R^{11}$ and $R^{12}$ represent aliphatic, aromatic, araliphatic or heterocyclic radicals.

Specific magenta-dye-forming coupler compounds which can be dried by the method of this invention include:

M-1

M-2

M-3

M-4

Couplers which form yellow dyes upon reaction with oxidized color developing agent are described in such representative U.S. Patents as Nos. 2,298,443; 2,875,057, 2,407,210; 3,265,506; 3,384,657; 3,408,194; 3,415,652; 3,447,928; 3,542,840; 4,046,575; 3,894,875; 4,095,983; 4,182,630; 4,203,768; 4,221,860; 4,326,024; 4,401,752; 4,443,536; 4,529,691; 4,587,205; 4,587,207 and 4,617,256, the disclosures of which are incorporated herein by reference.

Preferred yellow-dye-forming couplers are acylacetamides, such as benzoylacetanilides and pivalylacetanilides. Structures of such preferred couplers include:

-continued
and where $R^{13}$ is as defined above, $R^{14}$ is hydrogen or one or more halogen, lower alkyl (e.g. methyl, ethyl) or a ballast (e.g. alkoxy of 16 to 20 carbon atoms) group and X is a coupling off group.

Specific yellow-dye-forming coupler compounds which can be dried by the method of this invention include those of the formula:

wherein $R^{15}$ and $R^{16}$ are as defined below.

| Coupler No. | $R^{15}$ | $R^{16}$ |
|---|---|---|
| Y-1 | —NHCCH$_3$ (C=O) | —SO$_2$CH$_3$ |
| Y-2 | —NHCCH$_3$ (C=O) | —COCH$_3$ (C=O) |
| Y-3 | —NCCF$_3$ (C=O) | —COCH$_3$ (C=O) |
| Y-4 | —CNH$_2$ (C=O) | —H |
| Y-5 | —CNHCH$_2$CH$_2$OH (C=O) | —H |
| Y-6 | —NHCCH$_3$ (C=O) | —H |
| Y-7 | —NHSO$_2$CH$_3$ | —COCH$_3$ (C=O) |
| Y-8 | —NHCCF$_3$ (C=O) | —COCH$_3$ (C=O) |
| Y-9 | —CN(CH$_3$)$_2$ (C=O) | —H |
| Y-10 | —CN(CH$_3$)(C$_6$H$_5$) (C=O) | —H |
| Y-11 | —SO$_2$CH$_3$ | —H |
| Y-12 | —CNHCH$_3$ (C=O) | —H |
| Y-13 | —CH$_2$NHCCH$_3$ (C=O) | —H |

-continued

| Coupler No. | $R^{15}$ | $R^{16}$ |
|---|---|---|
| Y-14 | −CNH−⟨benzene ring⟩−SO$_2$NH$_2$ (with C=O) | −H |
| Y-15 | −CN−⟨tetrahydropyran ring with O⟩ (with C=O) | −H |
| Y-16 | −NHCCH$_3$ (with C=O) | −SO$_2$NHCH$_2$CH$_2$OH |
| Y-17 | −CNH−⟨pyridine ring with N⟩ (with C=O) | −H |
| Y-18 | −CNHNHCNH$_2$ (with two C=O) | −H |

Figure 1:
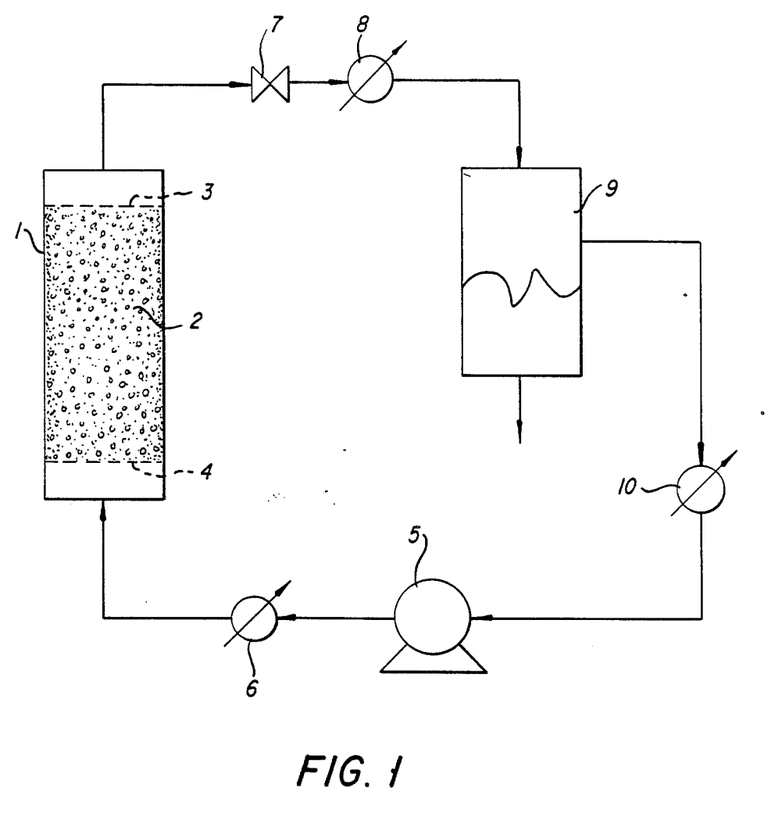
FIG. 1 is a schematic diagram illustrating the process of this invention.

FIG. 1 is a schematic diagram illustrating the process of this invention. As shown in the figure, extraction column 1 is packed with small particles 2 of a photographic coupler, or similar solid material, that are maintained in position by upper and lower retaining screens 3 and 4, respectively. Particles 2 contain occluded organic liquid from a prior crystallization step. Circulating pump 5 circulates carbon dioxide in a super-critical state through heat exchanger 6, which adjusts the temperature to the desired level, and then through extraction column 1. In extraction column 1, the supercritical carbon dioxide extracts the occluded organic liquid. After exiting from extraction column 1, the supercritical carbon dioxide, now rich in organic liquid, passes through pressure let-down valve 7, which reduces the pressure to a value favorable for separation, then through heat exchanger 8, which adjusts the temperature to a level suitable for separation, and into separation unit 9. In separation unit 9, the organic liquid is separated from the carbon dioxide and discharged from the bottom of the unit, while the carbon dioxide which exits from separatoor unit 9 passes through heat exchanger 10, which functions to liquefy it, and then to circulating pump 5 to be again circulated through the process.

The invention is further illustrated by the following examples of its practice.

EXAMPLE 1

In this example, the process of this invention was employed to remove occluded toluene from the yellow-dye-forming photograhic color coupler compound identified hereinabove as Coupler Y-1.

Ten grams of Coupler Y-1 in a finely-divided particulate form that was wet with fifty percent by weight of occluded toluene, was positioned in the center of an extractor consisting of a high-pressure tube whose end caps contained sintered metal disks to prevent entrainment of the solid out of the extractor. Glass wool was placed between the sintered disks and the sample to reduce the effective volume of the extractor, so that usage of material for each experiment was minimized. Carbon dioxide under supercritical conditions of 35° C. and a pressure of 81.6 atmospheres was admitted to the extractor and caused to percolate through the bed of wet coupler so as to extract the toluene. The resulting mixture of carbon dioxide and toluene was expanded to atmospheric pressure across a steam-heated regulating valve and thereafter passed over two water saturation columns and through a wet-test meter for measurement of the volumetric flow rate. After the sample had been extracted for a measured period of time, the extractor was vented and the end caps and glass wool were removed. The sample was then incrementally extruded with a piston and sectioned and toluene analysis in each section was carried out by gas chromatography. The concentration profile of toluene remaining in the solid was then integrated.

Figure 2:
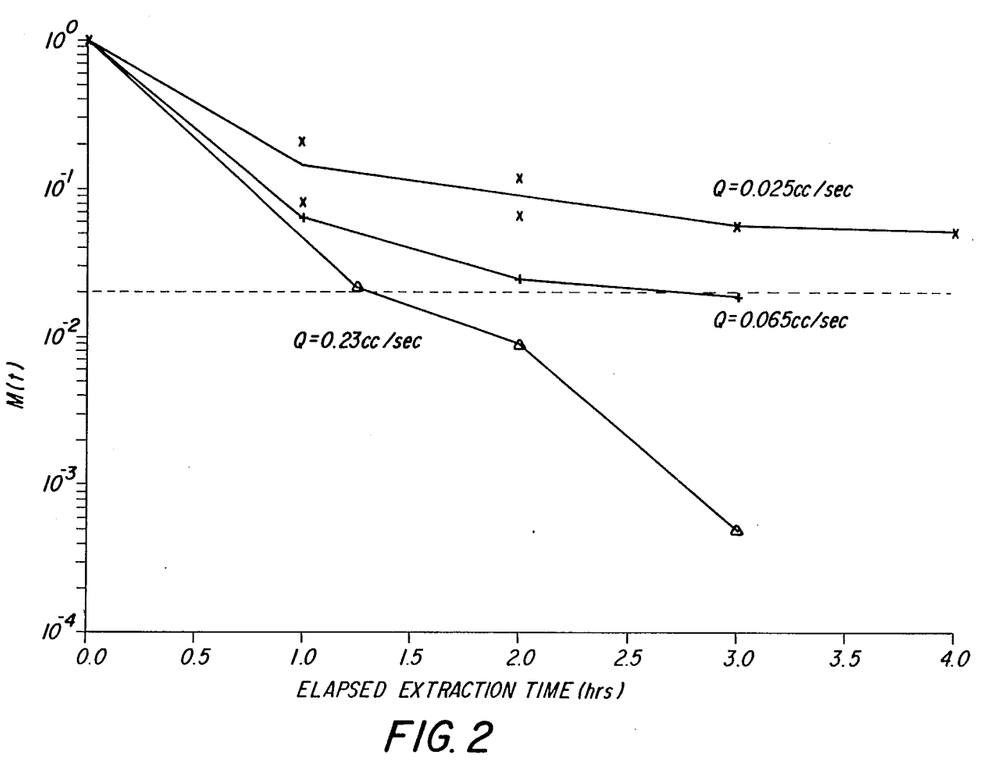
FIG. 2 is a plot illustrating the rate at which occluded toluene is extracted from a magenta-dye-forming photographic coupler utilizing the process of this invention.

The results obtained are summarized in FIG. 2, which is a plot of the logarithm of the decrease in integral toluene mass contained in the solid, nondimensionalized by the initial toluene mass present, against extraction time in hours for three different volumetric superficial flow rates. The broken line in FIG. 2 denotes a purity specification on the amount of toluene allowed in the final product of one percent. The symbol Q in FIG. 2 represents the volumetric flow rate in cubic centimeters per second, while the symbol M(t) is defined by the equation:

$$M(t) = \log_{10} \frac{\text{toluene mass in solid at time } t}{\text{initial toluene mass}}$$

The extraction of toluene is complete, that is, within specification, after three hours for all but the lowest volumetric flow rate. In contrast, the time required to dry Coupler Y-1 to within specification of less than one weight percent of toluene is approximately one day for a rotary batch processor and approximately two weeks for a rotatry-cone dryer. The rotary batch processor is described, for example, in U.S. Pat. Nos. 3,020,025, 3,250,321, and 3,285,330. A dryer of this type which is commercially available is the PORCUPINE processor from The Bethlehem Corporation, Bethlehem, Pa. A rotary-cone dryer is described, for example, in Section 20–46 of the Chemical Engineers' Handbook, Fifth Edition, McGraw-Hill Book Company, 1973.

Coupler Y-1 that had been dried by the process of this inventin was found to be satisfactory in all respects for use in the manufacture of photographic materials.

EXAMPLE 2

In this example, the process of this invention was employed to remove occluded toluene from the magenta-dye-forming photographic color coupler compound identified hereinabove as Coupler M-1.

Figure 3:
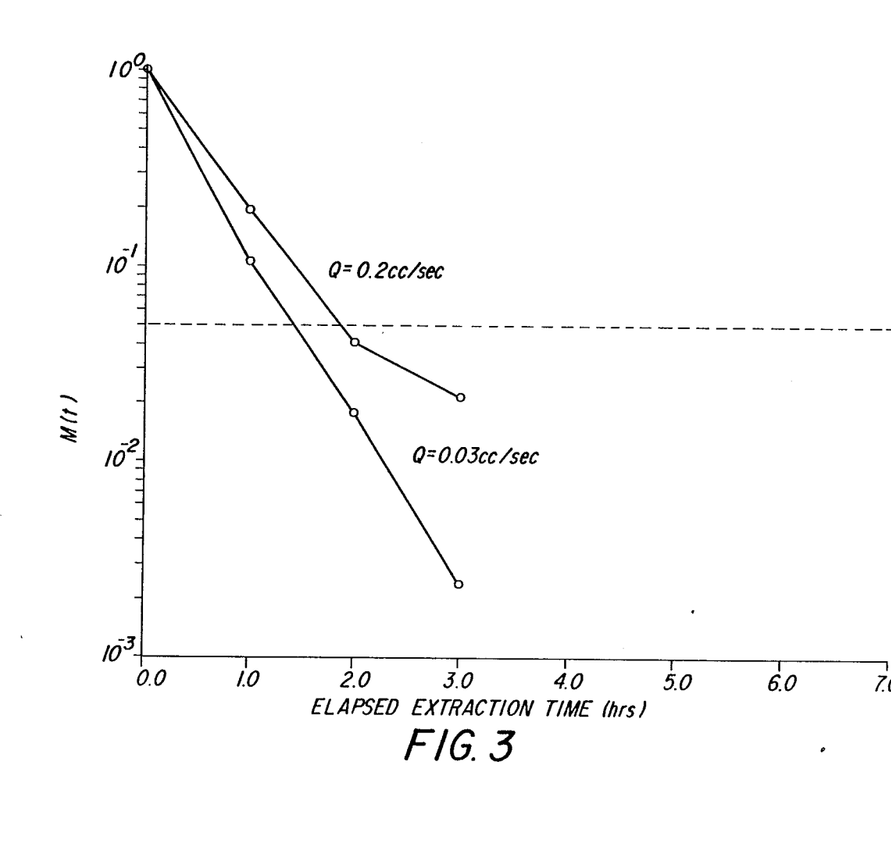
FIG. 3 is a plot illustrating the rate at which occluded toluene is extracted from a yellow-dye-forming photographic coupler utilizing the process of this invention.

The procedure was carried out in the same manner as in Example 1, but using two different volumetric flow rates. Coupler M-1 initially contained eighteen percent by weight of occluded toluene. The results obtained are shown in FIG. 3, where the broken line represents the one percent purity requirement on toluene. In this Figure, extraction rate is inversely related to flow rate, apparently due to flow channelling within the bed. As in Example 1, the sample meets the purity requirements in three hours. In contrast, the time required to dry Coupler M-1 to within specification of less than one weight percent of toluene is three to four days for a rotary batch processor and approximately four weeks for a rotary-cone dryer.

Coupler M-1 that had been dried by the process of this invention was found to be satisfactory in all respects for use in the manufacture of photographic materials.

The morphology of the coupler dried by extraction with supercritical carbon dioxide is very similar to that of the wet material before it is extracted. Since the extractant and extractate are miscible, surface tension does not affect the structure of the solid. Coupler Y-1 exits the extractor as a free-flowing powder, while Coupler M-1 exits the extractor as small, plate-shaped chunks. The balling and agglomeration problems of conventional dryers are effectively avoided.

EXAMPLE 3

Example 1 was repeated except that Coupler Y-1 had an initial concentration of 28 percent by weight of a mixture of toluene and heptane and the extraction was continued for two hours. At the end of this time, the total combined concentration of toluene and heptane had been reduced to 0.4 percent by weight.

EXAMPLE 4

Example 1 was repeated, except that Coupler Y-1 had an initial concentration of 28 percent by weight of a mixture of toluene and heptane, the extraction was conducted at 25° C. and 82 atmospheres with carbon dioxide in the liquid state, and the extraction was continued for four hours. At the end of this time, the total combined concentration of toluene and heptane had been reduced to 0.02 percent by weight.

EXAMPLE 5

Additional photographic addenda which have been subjected to extraction by the process of this invention with fully satisfactory results are listed in the following table, which also provides a brief description of their photographic function.

TABLE 1

| Addendum Number | Chemical Name of Addendum | Photographic Function |
| --- | --- | --- |
| I | 2-(p-(4-benzyloxyphenylsulfonyl)-phenoxy)-2'-chloro-5'-hexadecylsulfonamido-2-pivaloylacetanilide | Yellow image coupler |
| II | 2-(4-(4-hydroxyphenylsulfonyl)-phenoxy)-2'-chloro-5'-hexdecylsulfonamido-2-pivaloylacetanilide | Yellow image coupler |
| III | 6-methyl-3-(1-(4-nitrophenoxy)tridecyl-(-7h-1,2,4-triazolo-(3,4-B)-(1,3,4)thiadiazine | Magenta coupler intermediate |
| IV | 2,5-dihydroxy-4-(2-octadecyl)-benzenesulfonic acid sodium salt | Agent which alters shape of sensitometric curve of photographic emulsion |
| V | 3-butyltetrahydro-5(2h)-[3-(3-butyl-tetrahydro-1(2h)-carboxymethyl-2,4,6-trioxo-5(2h)-pyrimidinylidene)-1-propenyl]-2,4,6-trioxo-1(2h)-pyrimidine acetic acid | Magenta absorbing dye |
| VI | 1-[3-carboxy-5-hydroxyl-1-(p-sulfophenyl)pyrazolyl]-3-[3-carboxy-5-oxo-1-(p-sulfophenyl)-pyrazolinylidene]-propene disodium ditriethylamine salt | Magenta absorbing dye |
| VII | 2-(5-acetyl-4-(5-(5-acetyl-3-hydroxy-2-(2,5-disulfophenyl)-2,4-pyrazol-4-yl)-2,4-pentadienylidine)-2,4-dihydro-3-oxopyrazol)-1,4-benzenedisulfonic acid pentasodium salt | Cyan absorbing dye |
| VIII | p-(3-methyl-4-(3-methyl-1-(p-sulfophenyl)-5-oxo-2-pyrazolin-4-ylidene)methyl)-5-oxo-2-pyrazolin-1-yl)benzenesulfonic Acid Dipyridene Salt | Yellow absorbing dye |
| IX | 3-Ethyl-2,3-dihydro-2-(4-(2,4-dihydro-2-(-4-sulfophenyl)-3H-pyrazol-3-one-4-ylidene)but-2-ene-1-ylidene)-5-benzoxazolesulfonic Acid Disodium Salt | Magenta absorbing dye |
| X | Anhydro-5-chloro-2-{ethyl-3-[5-phenyl-3-(3-sulfobutyl)-2-benzoxazolinylidene[propenyl}-3-(sulfopropyl)benzoxazolium | Magenta sensitizing dye |

TABLE 1-continued

| Addendum Number | Chemical Name of Addendum | Photographic Function |
|---|---|---|
| | hydroxide Triethylamine Salt | |
| XI | Anhydro-5-chloro-3(3-sulfopropyl)--2-methylbenzothiazolium Hydroxide | Intermediate for a magenta sensitizing dye |
| XII | 1,1-Bis(4-Di-p-tolyaminophenyl)-cyclohexane | Photoconductor |
| XIII | Bis(phthalocyanylalumuno)tetra-phenyldisiloxane | Pigment |

The photographic addenda listed in Table 1 were dried by an extraction process as described in Example 1, and the results obtained are summarized in Table 2. Unless otherwise noted, all extractions were performed at 35° C. and a pressure of 81.6 atomspheres. In Table 2, the term "initial concentration" refers to total combined concentration of all the organic liquids; the term "specification concentrations" refers to the maximum permissible concentration of organic liquid in the product; and the term "actual concentration" refers to the concentration of organic liquid present after extraction for the designated time.

As will be noted from the data in Table 2, in every case the extraction time was not more than four hours and in some instances as short as one hour. Conventional drying procedures take much longer to reach the same level of organic liquid. For example, to reach the same level by air drying requires 168 hours for V, 240 hours for IX, 96 hours for X, 96 hours for IX, 48 hours for XII and 96 hours for XII. Using a vacuum dryer required 192 hours for III and 96 hours for IV. Addendum I required 4 hours in a rotary batch processor or 70 hours in a rotary cone dryer. Addendum II requried 24 hours in a rotary batch processor or 120 hours in a

TABLE 2

| Addendum Number | Organic Liquid(s) | Initial Concentration (Wt %) | Specification Concentration (Wt %) | Time (hrs) | Actual Concentration (Wt %) |
|---|---|---|---|---|---|
| I | methanol acetone | 41 | 0.5 | 1 | 0.2 |
| II | heptane n-propyl acetate toluene | 61 | 2 | 1 | 1 |
| III | acetonitrile | 25 | 4 | 3 | 2 |
| III | acetone acetonitrile methylene chloride acetic acid toluene | 34 | 4 | 4 | 3 |
| IV | isopropyl alcohol acetic acid heptane | 13 | 1 | 2 | 0.7 |
| V | acetic acid pyridine isopropyl alcohol | 5 | 1 | 2 | 0.2 |
| VI | dimethylformamide methanol triethylamine acetone | 14 | 1 | 2 | 0 |
| VII | acetone methanol dimethylformamide | 23 | 8 | 4 | 1.8 |
| VIII | acetone isopropyl alcohol acetic acid pyridine triethylorthoformate | 7 | 1 | 2* | 0.9 |
| IX | dimethylformamide methanol acetone | 31 | 2 | 4 | 0.8 |
| X | isopropyl alcohol triethylamine ethyl acetate | 6 | 4 | 4 | <1 |
| XI | acetone N-methyl-2-pyrrolidinone butyronitrile | 27 | 0.5 | 4 | 0.1 |
| XII | acetone xylenes acetic acid methanesulfonic acid cyclohexanone | 28 | 0.2 | 4 | 0.1 |
| XIII | pyridine acetone | 32 | 4 | 4 | 1 |

*In this case, the extraction was carried out at 50° C. and 272 atmospheres.

rotary cone dryer. Addendum VIII required 120 hours in rotary cone dryer.

The results obtained in the above examples are surprising. It was unexpected that such substantial amounts of orgnic liquid could be removed in such short periods of time, and also unexpected that the properties of the addenda which render them capable of photographic use would not be in any way adversely affected by the process.

It should be noted that the process of this invention is a drying process for removal of substantial amounts of occluded organic liquid, as distinguished from a process for extracting from a solid a desired component which is present in only very small amounts. In the process of this invention, the component which is most valuable is the solid material, and it is desired to dry such material without adversely affecting its physical or chemical properties. The initial product may contain large amounts of occluded organic liquid, up to as much as two parts of liquid per part by weight of solid or more. The product of the process is the solid with only very small amounts of occluded organic liquid, such as one weight percent or less. Thus, the purpose and objectives of the process of this invention are clearly different than a process such as that of Schultz, U.S. Pat. No. 3,966,981, in which product with a residual solvent content of a few hundred ppm is extracted to reduce residual solvent content to a few ppm.

The process of this invention has many advantages over the drying processes now in commercial use for the drying of solid photographic addenda. For example, it is carried out quickly and easily in simple equipment that can be operated at moderate cost. It permits the solvents associated with the solid photographic addenda to be easily recovered by separation from the carbon dioxide, and thereby avoids the problems associated with emission of potentially hazardous solvents from conventional dryers. It utilizes an extractant which is environmentally safe and easily handled. It is effective with a wide range of organic liquids and functions over a very broad range of concentrations of occluded liquid. It provides a product that is capable of meeting the demanding requirements of the photographic art with respect to both physical and chemical characteristics.

The invention has been described in detail with particular reference to preferred embodiments thereof, but it will be understood that variations and modifications can be effected within the spirit and scope of the invention.

We claim:

1. A method of treating a solid photographic addendum to remove occluded organic liquid therefrom, said organic liquid being present in an amount of from about 0.04 parts to about 2 parts per part by weight of said solid addendum; which method comprises the steps of:
    (1) contacting said solid photographic addendum in particulate form with an extractant composed of carbon dioxide in liquid form or in the form of a supercritical fluid for a time sufficient to extract said organic liquid, said solid addendum being insoluble in said extractant and said organic liquid being soluble in said extractant; and
    (2) recovering said solid addendum in a substantially dry state.

2. A method of treating a solid photographic addendum to remove occluded organic liquid therefrom, said organic liquid being present in an amount of from about 0.04 parts to about 2 parts per part by weight of said solid addendum; which method comprises the steps of:
    (1) contacting said solid photographic addendum in particulate form with an extractant composed of carbon dioxide in liquid form or in the form of a supercritical fluid for a time sufficient to extract said organic liquid, said solid addendum being insoluble in said extractant and said organic liquid being soluble in said extractant;
    (2) recovering said solid addendum in a substantially dry state.
    (3) separating said organic liquid from said extractant; and
    (4) recycling said extractant to step (1).

3. A method of treating a solid photographic addedum to remove occluded organic liquid therefrom, said organic liquid being present in an amount of from about 0.04 parts to about 2 parts per part by weight of said solid addendum; which method comprises the steps of:
    (1) contacting said solid photographic addendum in particulate form with an extractant composed of carbon dioxide in liquid form or in the form of a supercritical fluid for a time sufficient to extract said organic liquid to a level of below 0.02 parts per part by weight of said solid addendum, said solid addendum being insoluble in said extractant and said organic liquid being soluble in said extractant; and (2) recovering said solid addendum in a substantially dry state.

4. A method as claimed in claim 1 wherein said solid photographic addendum is a photographic color coupler.

5. A method as claimed in claim 1 wherein said solid photographic addendum is a photographic dye.

6. A method as claimed in claim 1 wherein said organic liquid is toluene.

7. A method as claimed in claim 1 wherein said organic liquid and said extractant are fully miscible.

8. A method as claimed in claim 1 wherein said step of contacting is brought about by percolating said extractant through a bed composed of particles of said solid photographic addendum.

9. A method as claimed in claim 1 wherein the time of contacting is up to four hours.

10. A method as claimed in claim 1 wherein said organic liquid is toluene and said solid photographic addendum is a magenta-dye-forming coupler compound of the formula:

11. A method as claimed in claim 1 wherein said organic liquid is toluene and said solid photographic addendum is a yellow-dye-forming coupler compound of the formula:

12. In a process for the manufacture of a solid chemical material, that is useful as an addendum in a photographic system, including the step of separating said material from an organic liquid in a particulate form that is wet with occluded organic liquid in an amount of from about 0.04 parts to about 2 parts per part by weight, the improvement which comprises drying said wet material by a method comprising the steps of (1) contacting said material with an extractant composed of carbon dioxide in liquid form or in the form of a supercritical fluid for a time sufficient to extract said organic liquid, said material being insoluble in said extractant and said organic liquid being soluble in said extractant, and (2) recovering said material in a substantially dry state.

* * * * *